(12) United States Patent
Ciceri et al.

(10) Patent No.: US 9,062,018 B2
(45) Date of Patent: Jun. 23, 2015

(54) CRYTALLINE FORM OF 13-[(N-TERT-BUTOXYCARBONYL)-2'-O-HEXANOYL-3-PHENYLISOSERINYL]-10-DEACETYLBACCATIN III

(75) Inventors: Daniele Ciceri, Milan (IT); Andrea Gambini, Milan (IT); Maurizio Ricotti, Milan (IT); Nicola Sardone, Milan (IT)

(73) Assignee: Indena S.p.A, Milan (IT)

( * ) Notice: Subject to any disclaimer, the term of this patent is extended or adjusted under 35 U.S.C. 154(b) by 172 days.

(21) Appl. No.: 13/882,014

(22) PCT Filed: Oct. 27, 2011

(86) PCT No.: PCT/EP2011/068835
§ 371 (c)(1),
(2), (4) Date: May 20, 2014

(87) PCT Pub. No.: WO2012/055952
PCT Pub. Date: May 3, 2012

(65) Prior Publication Data
US 2014/0303240 A1    Oct. 9, 2014

(30) Foreign Application Priority Data
Oct. 29, 2010 (EP) .................................... 10189373

(51) Int. Cl.
*C07D 305/00* (2006.01)
*C07D 305/14* (2006.01)
*C07D 305/06* (2006.01)
*C07D 493/04* (2006.01)

(52) U.S. Cl.
CPC ............ *C07D 305/14* (2013.01); *C07D 305/06* (2013.01); *C07D 493/04* (2013.01)

(58) Field of Classification Search
CPC ........................... C07D 305/14; C07D 305/06
USPC .................................................. 549/510, 511
See application file for complete search history.

(56) References Cited

U.S. PATENT DOCUMENTS

2009/0130163 A1   5/2009  Desai et al.
2009/0275762 A1  11/2009  Liao et al.

FOREIGN PATENT DOCUMENTS

| RU | 2284328 C2 | 11/2002 |
| WO | 03045953 A1 | 11/2002 |
| WO | 2006089207 | 8/2006 |
| WO | 2009126175 | 10/2009 |

*Primary Examiner* — Raymond Covington
(74) *Attorney, Agent, or Firm* — Price Heneveld LLP

(57) ABSTRACT

A crystalline from of 13-[(N-tert-butoxycarbonyl)-2'-O-hexanoyl-3-phenylisoserinyl]-10-deacetylbaccatin III.

17 Claims, 4 Drawing Sheets

CRYSTALLINE FORM OF 13-[(N-TERT-BUTOXYCARBONYL)-2'-O-HEXANOYL-3-PHENYLISOSERINYL]-10-DEACETYLBACCATIN III

FIELD OF INVENTION

The present invention relates to a new crystalline form of 13-[(N-tert-butoxycarbonyl)-2'-O-hexanoyl-3-phenylisoserinyl]-10-deacetylbaccatin III hereinafter referred to as compound (1). Compound (1), previously described in US 2009/0130163 and WO 2009/126175, acts to inhibit cell proliferation and migration. It can be effectively incorporated in medical devices such as stents, in order to reduce the incidence of post angioplasty closure of the vessels. Compound (1) may also be used as medicament against tumors.

BACKGROUND OF THE INVENTION

US 2009/0130163 and WO 2009/126175 report various possible applications of compound (1) but do not disclose any of its physical properties. Probably due to the presence of the highly flexible pentyl-carbonyl moiety in 2'-O-position, compound (1) cannot be easily crystallized and hence is usually prepared in an amorphous form. However this form showed problems of chemical stability during ICH stability studies, mainly with respect to an impurity stemming from oxidation of the 10-position of the baccatin core. Since crystalline materials have a lower Gibbs free energy compared to amorphous forms it is expected for a crystalline material a lower decomposition rate and hence a better behaviour during stability studies. Thus it is desirable to find a crystalline form of compound (1) which is chemically and thermodynamically stable. A method for preparing such solid form of compound (1) continually and constantly is also a prerequisite for the development of a robust manufacturing process.

DETAILED DESCRIPTION

Figure 1:
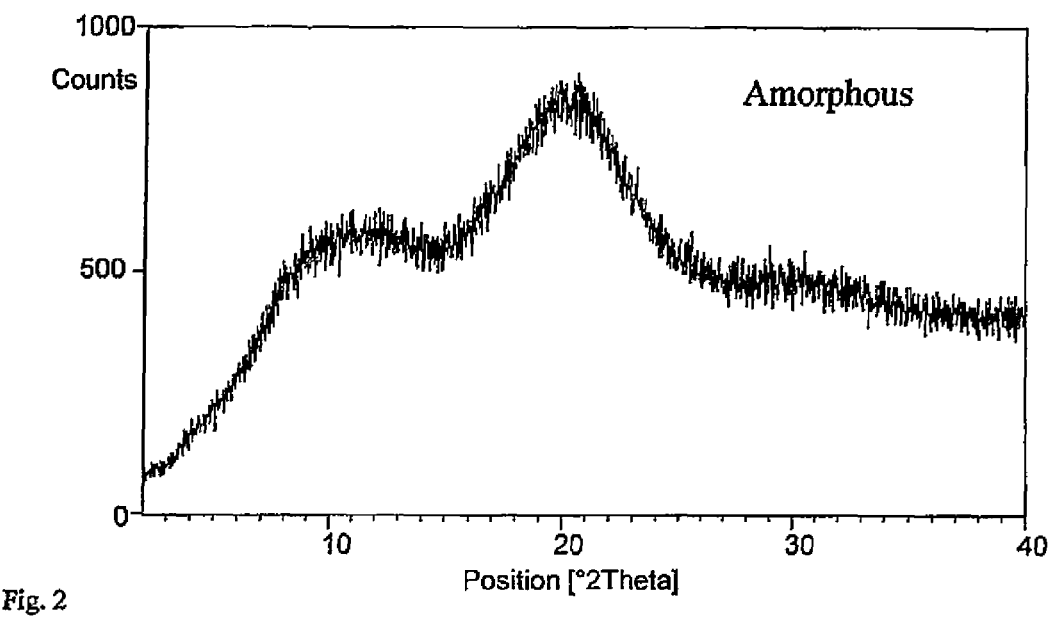
FIG. 1 is a X-ray Powder diffraction pattern of an amorphous sample.

It has now been found that compound (1) can exist in a crystalline form. Thus, according to a first aspect, the present invention provides a crystalline form of 13-[(N-tert-butoxycarbonyl)-2'-O-hexanoyl-3-phenylisoserinyl]-10-deacetylbaccatin III.

As known to the skilled person, there are measuring methods available to verify whether a solid is in a crystalline form or not. Crystallinity can be detected e.g. by diffraction techniques such as X-ray powder diffraction or differential thermal analysis (e.g. for measuring melting and/or crystallization temperature).

In a preferred embodiment, the crystalline form of 13-[(N-tert-butoxycarbonyl)-2'-O-hexanoyl-3-phenylisoserinyl]-10-deacetylbaccatin III is crystalline Form A. Accordingly, the polymorph, called "Form A", is a preferred subject of the present invention, along with the process for producing it.

Preferably, the crystalline Form A of 13-[(N-tert-butoxycarbonyl)-2'-O-hexanoyl-3-phenylisoserinyl]-10-deacetylbaccatin III has an XRPD diffractogram characterized by the following peaks: 6.1, 9.1, 10.1, 10.6, 11.7, 13.0, 18.5, 19.8, 22.0 deg 2-theta±0.2°. More preferably, the crystalline Form A additionally has the following peaks in the XRPD diffractogram: 9.8, 14.0, 15.4, 16.4, 17.5, 17.8, 19.2, 20.6, 22.7, 24.1, 25.4, 27.0, 28.0, 30.2, 313, 31.7, 34.6 deg 2-theta±0.2°.

In a preferred embodiment, crystalline Form A is a hydrate. Preferably, the hydrate of the crystalline Form A has a water content of up to 4.0 wt %, more preferably of from 1.0 wt % to 2.5 wt %. In a preferred embodiment, the hydrate of the crystalline Form A is a mono-hydrate. In a preferred embodiment, the crystalline Form A has a melting point of 130±2° C., measured as the peak temperature by differential thermal analysis at a heating rate of 10° C./min. In a preferred embodiment, Form A is a monohydrated form which contains about 2% of water and/or melts at about 130° C. In a preferred embodiment, Form A is a hydrate containing crystallization water which is released in the temperature range of from 70-120° C. as measured by differential thermal analysis at a heating rate of 10° C./min, in an amount of about 1.0 to 1.5 wt %.

Preferably, the crystalline Form A has an FTIR-ATR spectrum showing absorption frequencies at 3444, 3265, 2971, 2940, 1732, 1697, 1367 1240, 1157, 1063, 973 756, 704 $cm^{-1}±2 cm^{-1}$. More preferably, the crystalline Form A additionally has the following peaks in the FTIR-ATR spectrum: 3063, 2902, 2875, 1641, 1603, 1586, 1538, 1497, 1454, 1316, 1277, 1023, 946, 918, 884, 849, 802, 776, 644, 609, 577 $cm^{-1}±2 cm^{-1}$.

According to a further aspect, the present invention provides the crystalline form of 13-[(N-tert-butoxycarbonyl)-2-O'-hexanoyl-3-phenylisoserinyl]-10-deacetylbaccatin III as described above for use as a medicament. Preferably, the crystalline form, in particular crystalline Form A, can be used as a medicament for inhibiting cell proliferation and migration, reducing the incidence of post angioplasty closure of the vessels, and/or tumor treatment.

According to a further aspect, the present invention provides a process for preparing the crystalline form of 13-[(N-tert-butoxycarbonyl)-2'-O-hexanoyl-3-phenylisoserinyl]-10-deacetylbaccatin III as described above, which comprises stirring 13-[(N-tert-butoxycarbonyl)-2'-O-hexanoyl-3-phenylisoserinyl]-10-deacetylbaccatin III in a mixture of an alcoholic solvent with water. Preferably, the stirring time is at least 2 hours, more preferably at least 12 hours. In a preferred embodiment, 13-[(N-tert-butoxycarbonyl)-2'-O-hexanoyl-3-phenylisoserinyl]-10-deacetylbaccatin III, which is preferably in the amorphous form, is at least partly dissolved in the alcoholic solvent, followed by mixing the alcoholic solution with water, and stirring the mixture of alcoholic solvent and water. Preferably, the mixture is stirred at a temperature in the range of from 0 to 45° C., more preferably at room temperature. Preferably, the alcoholic solvent is methanol, ethanol or a mixture thereof. Preferably, the volumetric ratio of alcoholic solvent to water is between 0.3 and 0.6.

The importance of the crystalline form of compound (1), preferably Form A, rests primarily in the chemical stability of compound (1). Oxidation of the 10-position of the baccatin core is prevented in this new form. Ease of isolation by means of filtration or centrifugation is another asset of Form A. As already indicated above, according to a preferred embodiment of the invention, the preparation of Form A can be accomplished dissolving raw compound (1) (e.g. in its amorphous form) in a suitable amount of alcoholic solvent, preferably methanol or ethanol, and adding this solution to a suitable amount of water. Slurring the resulting mixture at a variable temperature, preferably 0-45° C., most preferably at about room temperature for at least 12 hours will lead to Form A. The typical volumetric ratio of alcoholic solvent and water is 0.3-0.6.

Characterization

X-ray powder diffraction (XRPD), Thermogravimetry and differential thermal analysis (TG/DTA) and Fourier-transform infrared spectroscopy (FTIR) allow differentiating Form A from the amorphous phase of compound (1).

X-ray Powder Diffraction (XRPD)

X-ray powder diffraction patterns were collected on a Philips PW1800 Diffractometer. The x-ray generator was operated at 45 kV and 35 mA, using the Cu Kα line as the radiation source. The sample was packed on a suitable slit and the irradiated length was 10 mm. Data were collected between 2 and 65 deg 2-theta with a step size of 0.02 deg 2-theta.

Thermogravimetry and Differential Thermal Analysis (TG/DTA)

The Thermaogravimetry and Differential Thermal Analysis (TG/DTA) analyses were performed using a Seiko TG/DTA6200 simultaneous system using open aluminum pans (40 µl volume). The TG/DT signals were recorded from 30 to 300° C. with linear heating rate (10° C./min) under a 200 ml/min nitrogen flow. About 10 mg of powder was used for each measurement.

Fourier-Transform Infrared Spectroscopy (FTIR)

The infrared spectra were recorded with ATR technique using a Fourier-transform spectrometer Perkin Elmer Spectrum One. The spectra were the result of the acquisition and transformation of 16 co-added scans in the 4000-550 $cm^{-1}$ spectral region at a resolution of 4 $cm^{-1}$.

Amorphous

The x-ray powder diffraction pattern of an amorphous sample (FIG. 1, 2≤2θ≤40° angular range) shows absence of diffraction peaks and a broad noise typical of an amorphous sample.

Figure 2:
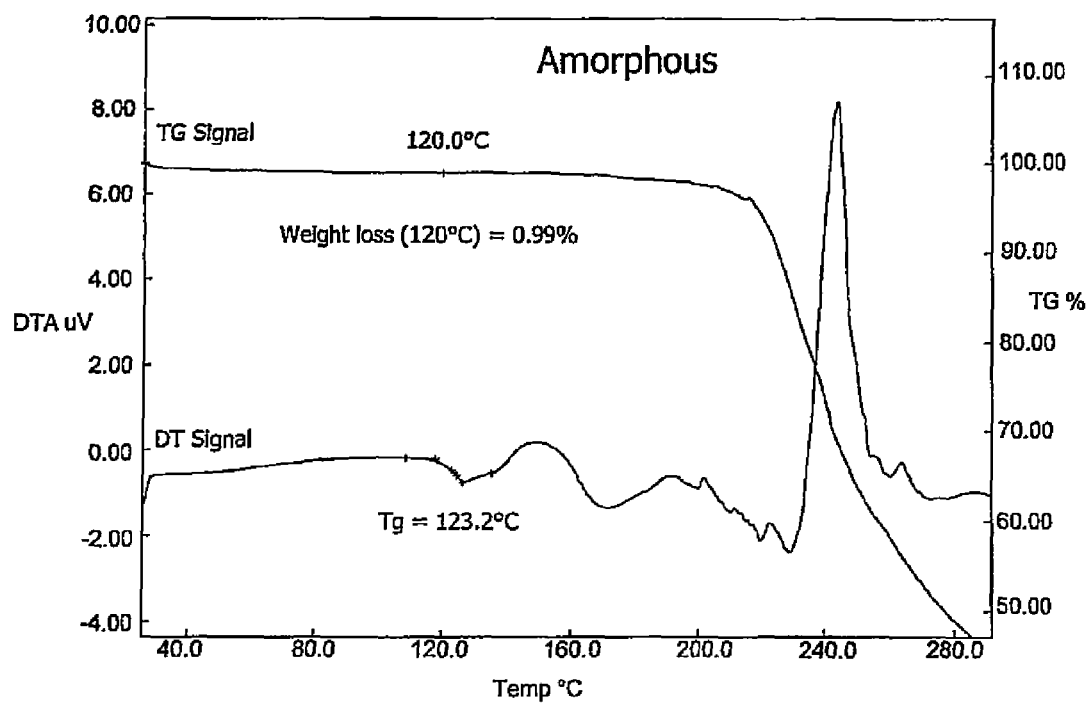
FIG. 2 is a Thermogravimetry and Differential Thermal Analysis of an amorphous sample.

The TG/DT analysis of an amorphous sample (FIG. 2) shows a DT profile characterized by a glass transition at about 123° C. In the TG profile, a weight loss of about 1.0% from 30 to 120° C. due to release of residual moisture is followed by a massive weight loss which takes place upon 200° C. due to a degradative reaction.

Figure 3A:
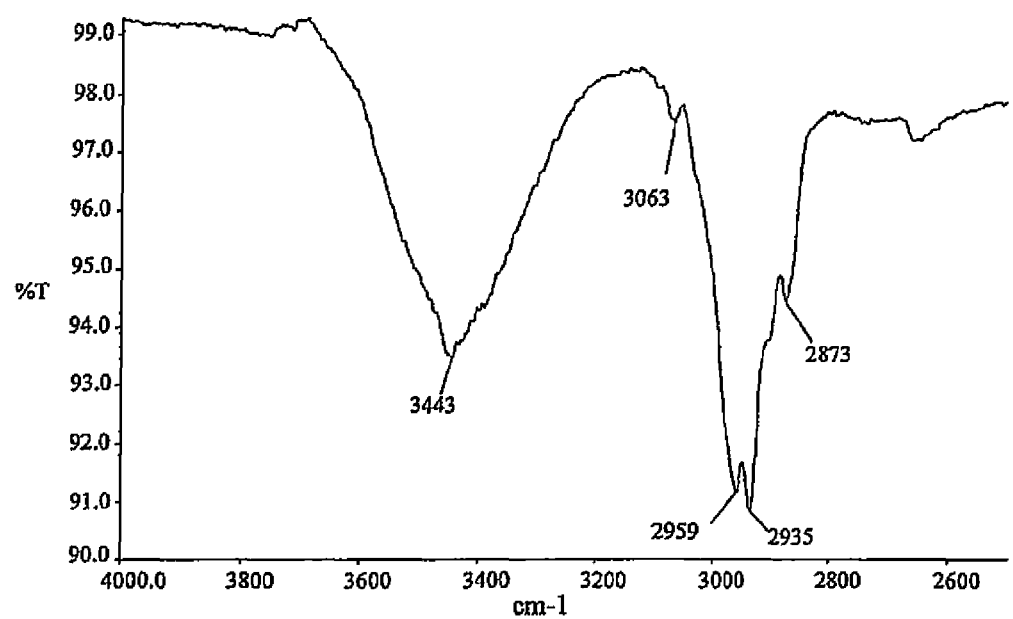
FIGS. 3a and 3b are Fourier-Transformed Infrared Spectroscopy spectrum of an amorphous sample in the 4000-2500 $cm^{-1}$ spectral range and the 1900-550 $cm^{-1}$ spectral range respectively.

The FTIR-ATR spectrum of an amorphous sample is shown in FIGS. 3a (the 4000-2500 $cm^{-1}$ spectral range) and 3b (the 1900-550 $cm^{-1}$ spectral range). It shows absorption frequencies at 3443, 2959, 2935, 1707, 1496, 1453, 1367, 1242, 1159, 1068, 1024, 982, 776, 708 $cm^{-1}$±2 $cm^{-1}$.

Form A

Preferred embodiments of crystalline Form A are discussed below by making reference to XRPD, TG/DT, and FTIR-ATR measurements shown in FIGS. 4 to 6b.

The x-ray powder diffraction pattern of Form A (FIG. 4, 2≤2θ≤40° angular range) shows a crystalline structure with useful distinctive reflections at approximately 6.1, 9.1, 9.8, 10.1, 10.6, 11.7, 13.0, 14.0, 15.4, 16.4, 17.5, 17.8, 18.5, 19.2, 19.8, 20.6, 22.0, 22.7, 24.1, 25.4, 27.0, 28.0, 30.2, 31.5, 31.7, 34.6 deg 2-theta.

Figure 4:
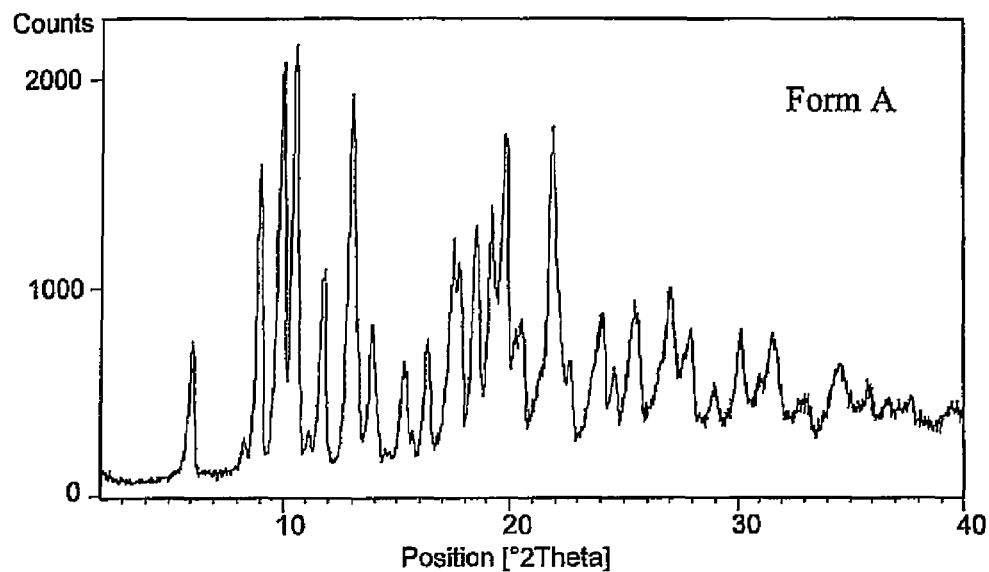
FIG. 4 is an X-ray Powder Diffraction pattern of crystalline Form A.

In a preferred embodiment, the crystalline form of 13-[(N-tert-butoxycarbonyl)-2-O'-hexanoyl-3-phenylisoserinyl]-10-deacetylbaccatin III has an X-ray powder diffraction pattern substantially in accordance with FIG. 4.

The TG/DT analysis of Form A (FIG. 5) shows a DT profile characterized by a weak endothermic signal below 70° C. due to release of residual moisture, associated to a weight loss (in the TG profile) of about 2.5%; an endothermic peak with maximum at about 82° C. due to release of crystallization water, associated to a weight loss (in the TG profile) of about 1.2% from 70 to 120° C. (coherent with an hydrate product); a melting peak with onset at about 123° C. and maximum at about 130° C. In the TG profile, the first progressive loss of weight is followed by a massive loss which takes place upon 180° C. due to a degradative reaction.

Figure 5:
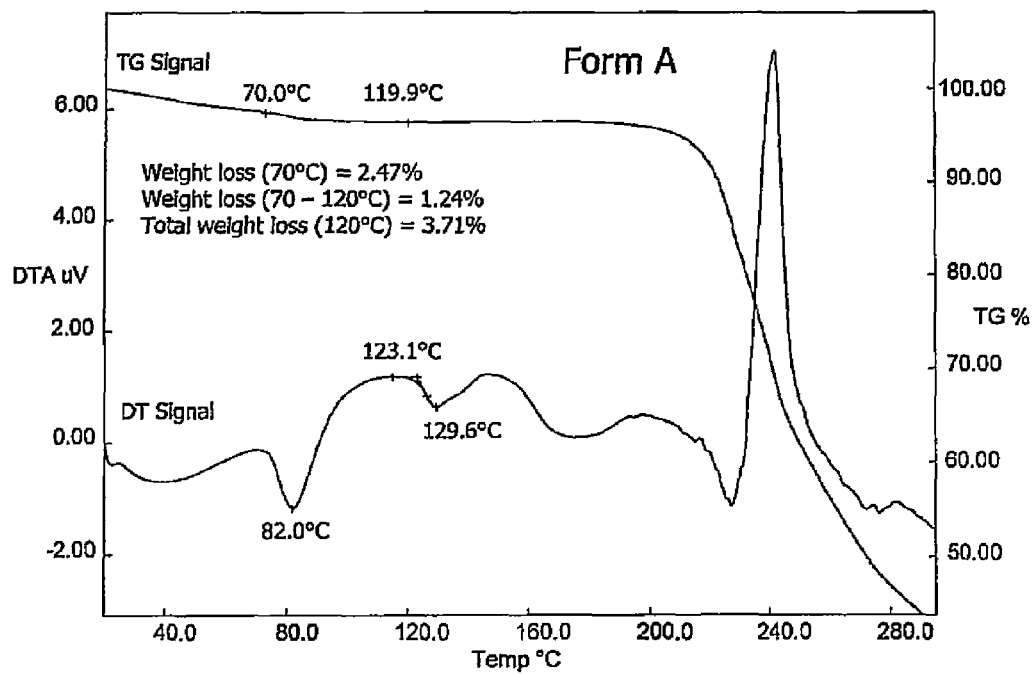
FIG. 5 shows a thermogravimetry and a thermal analysis of crystalline Form A.

In a preferred embodiment, the crystalline form of 13-[(N-tert-butoxycarbonyl)-2'-O-hexanoyl-3-phenylisoserinyl]-10-deacetylbaccatin III has a differential thermal analysis profile substantially in accordance with FIG. 5.

Figure 6A:
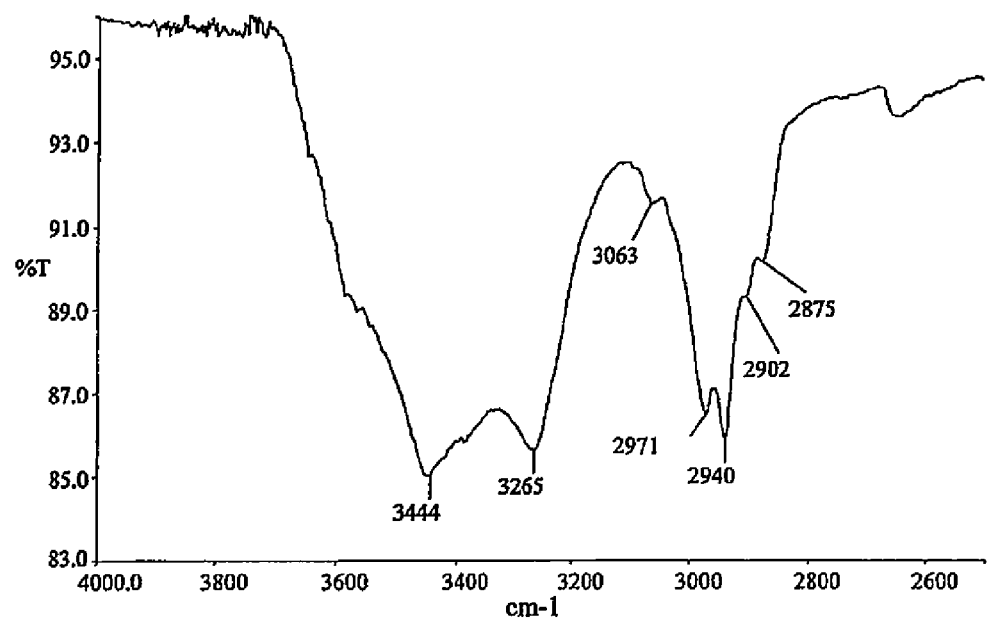
FIGS. 6a and 6b show Fourier-Transform Infrared Spectroscopy spectrums of crystalline Form A in the 4000-2500 $cm^{-1}$ spectral range and 1900-550 $cm^{-1}$ spectral range respectively.

The FTIR-ATR spectrum of Form A is shown in FIGS. 6a (the 4000-2500 $cm^{-1}$ spectral range) and 6b (the 1900-550 $cm^{-1}$ spectral range). It shows absorption frequencies at 3444, 3265, 3063, 2971, 2940, 2902, 2875, 1732, 1697, 1641, 1603, 1586, 1538, 1497, 1454, 1367, 1316, 1277, 1240, 1157, 1063, 1023, 973, 946, 918, 884, 849, 802, 776, 756, 704, 644, 609, 577 $cm^{-1}$.

Figure 6B:
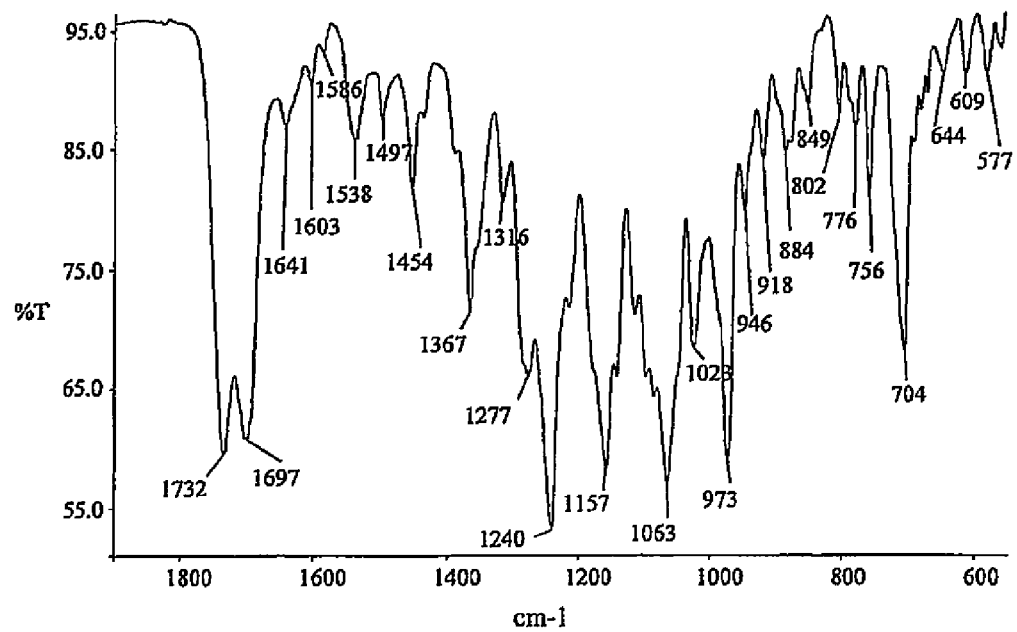

In a preferred embodiment, the crystalline form of 13-[(N-tert-butoxycarbonyl)-2-O'-hexanoyl-3-phenylisoserinyl]-10-deacetylbaccatin III has a FTIR-ATR spectrum substantially in accordance with FIGS. 6a and 6b.

The present invention is illustrated by the following examples, which are not intended to limit the effective scope of the claims:

Example 1

Preparation of Crystalline Form A

Amorphous compound (1) (10 g) (prepared as described in WO 2009/126175, example 2) was dissolved in ethanol (70 mL) at room temperature. The solution was added over 1 hour to purified water (140 mL) and the resulting slurry stirred at room temperature for 16 hours. The white solid was filtered off, washed with a 33% solution of ethanol in water and dried under vacuum at 40° C. for 16 hours affording compound (1) having the characteristic XRPD, TG/DTA and IR reported in FIGS. 4, 5 and 6 respectively.

Example 2

Stability data at 25±2° C. and 60±5% relative humidity of amorphous and Form A of compound (1). The packaging was the same for both solid forms (Amber glass vial+polyethylene bag+vacuum sealed PET/Aluminum/PE multilayer bag).

| Amourphous Form of compound (1) | | | |
|---|---|---|---|
| | T = 0 | 3 months | 6 months |
| Determinations | | | |
| HPLC assay (%) of compound (1) with reference to the anhydrous and solvent free basis | 99.7% | 99.0% | 98.9% |

-continued

Amourphous Form of compound (1)

Figure 3B:
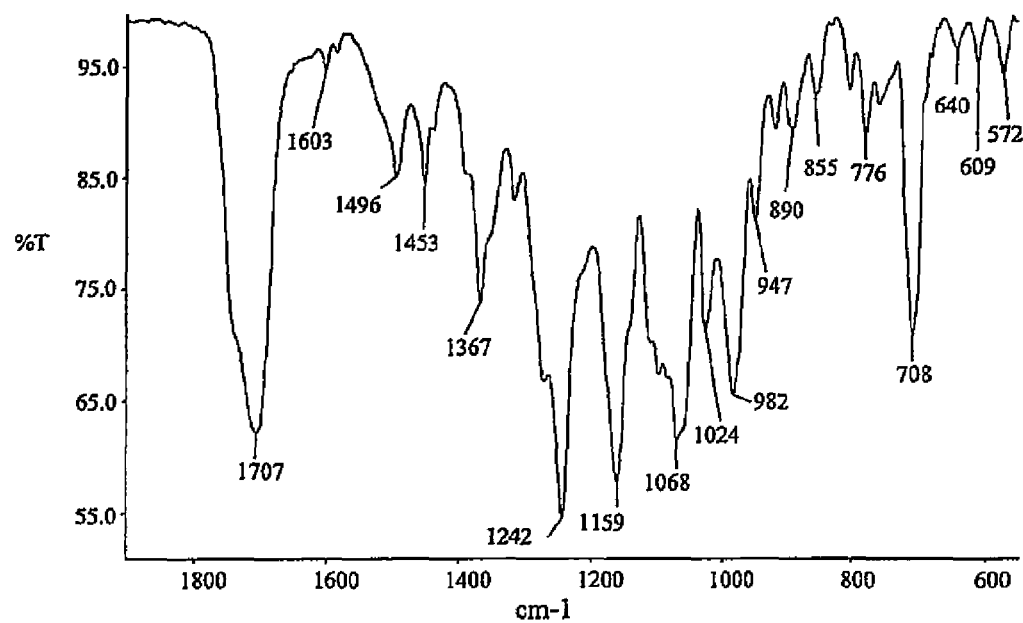

|  | T = 0 | 3 months | 6 months |
|---|---|---|---|
| IR identification | Complies with FIG. 3A-3-B | Complies | Complie |
| Specific optical rotation (°) (c = 1 ethanol, at 20° C.) | −46.0 | −46.3 | −46.0 |
| Potential impurity-HPLC (area %) | | | |
| 10-dehydro compound (1) | 0.29% | 0.36% | 0.53% |

Form A of compound (1)

|  | T = 0 | 3 months | 6 months |
|---|---|---|---|
| Determinations | | | |
| HPLC assay (%) of compound (1) with reference to the anhydrous and solvent free basis | 99.0% | 99.0% | 99.1% |
| IR identification | Complies with FIG. 6A-6-B | Complies | Complies |
| Specific optical rotation (°) (c = 1 ethanol, at 20° C.) | −46.2 | −46.3 | −46.3 |
| Potential impurity-HPLC (area %) | | | |
| 10-dehydro compound (1) | 0.29% | 0.29% | 0.29% |

What is claimed is:

1. A crystalline form of 13-[(N-tert-butoxycarbonyl)-2'-O-hexanoyl-3-phenylisoserinyl]-10-deacetylbaccatin III, which is crystalline Form A having an XRPD diffractogram characterized by the following peaks: 6.1, 9.1, 10.1, 10.6, 11.7, 13.0, 18.5, 19.8, 22.0 deg 2-theta±0.2°.

2. The crystalline form of 13-[(N-tert-butoxycarbonyl)-2'-O-hexanoyl-3-phenylisoserinyl]-10-deacetylbaccatin III of claim 1, additionally having the following peaks in the X-ray Powder Diffraction diffractogram: 9.8, 14.0, 15.4, 16.4, 17.5, 17.8, 19.2, 20.6, 22.7, 24.1, 25.4, 27.0, 28.0, 30.2, 31.5, 31.7, 34.6 deg 2-theta±0.2°.

3. The crystalline form of 13-[(N-tert-butoxycarbonyl)-2'-O-hexanoyl-3-phenylisoserinyl]-10-deacetylbaccatin III of the claim 1, wherein the crystalline Form A is a hydrate.

4. The crystalline form of 13-[(N-tert-butoxycarbonyl)-2'-O-hexanoyl-3-phenylisoserinyl]-10-deacetylbaccatin III of the claim 2, wherein the crystalline Form A is a hydrate.

5. The crystalline form of 13-[(N-tert-butoxycarbonyl)-2'-O-hexanoyl-3-phenylisoserinyl]-10-deacetylbaccatin III of claim 3, wherein the hydrate of the crystalline Form A has a water content of up to 4.0 wt %.

6. The crystalline form of 13-[(N-tert-butoxycarbonyl)-2'-O-hexanoyl-3-phenylisoserinyl]-10-deacetylbaccatin III of claim 5, wherein the hydrate of the crystalline Form A is a mono-hydrate.

7. The crystalline form of 13-[(N-tert-butoxycarbonyl)-2'-O-hexanoyl-3-phenylisoserinyl]-10-deacetylbaccatin III of claim 3, wherein the hydrate of the crystalline Form A is a mono-hydrate.

8. The crystalline form of 13-[(N-tert-butoxycarbonyl)-2'-O-hexanoyl-3-phenylisoserinyl]-10-deacetylbaccatin III of claim 1, wherein the crystalline Form A has a melting point of 130±2° C., measured as the peak temperature by differential thermal analysis at a heating rate of 10° C./min.

9. The crystalline form of 13-[(N-tert-butoxycarbonyl)-2'-O-hexanoyl-3-phenylisoserinyl]-10-deacetylbaccatin III of claim 2, wherein the crystalline Form A has a melting point of 130±2° C., measured as the peak temperature by differential thermal analysis at a heating rate of 10° C./min.

10. The crystalline form of 13-[(N-tert-butoxycarbonyl)-2'-O-hexanoyl-3-phenylisoserinyl]-10-deacetylbaccatin III of claim 7, wherein the crystalline Form A has a melting point of 130±2° C., measured as the peak temperature by differential thermal analysis at a heating rate of 10° C./min.

11. The crystalline form of 13-[(N-tert-butoxycarbonyl)-2'-O-hexanoyl-3-phenylisoserinyl]-10-deacetylbaccatin III of claim 8, wherein the crystalline Form A has a melting point of 130±2° C., measured as the peak temperature by differential thermal analysis at a heating rate of 10° C./min.

12. The crystalline form of 13-[(N-tert-butoxycarbonyl)-2'-O-hexanoyl-3-phenylisoserinyl]-10-deacetylbaccatin III of claim 1, wherein the crystalline Form A has an FTIR-ATR spectrum showing absorption frequencies at 3444, 3265, 2971, 2940, 1732, 1697, 1367, 1240, 1157, 1063, 973, 756, 704 $cm^{-1}$±2 $cm^{-1}$.

13. The crystalline form of 13-[(N-tert-butoxycarbonyl)-2'-O-hexanoyl-3-phenylisoserinyl]-10-deacetylbaccatin III of claim 3, wherein the crystalline Form A has an FTIR-ATR spectrum showing absorption frequencies at 3444, 3265, 2971, 2940, 1732, 1697, 1367, 1240, 1157, 1063, 973, 756, 704 $cm^{-1}$±2 $cm^{-1}$.

14. The crystalline form of 13-[(N-tert-butoxycarbonyl)-2'-O-hexanoyl-3-phenylisoserinyl]-10-deacetylbaccatin III of claim 6, wherein the crystalline Form A has an FTIR-ATR spectrum showing absorption frequencies at 3444, 3265, 2971, 2940, 1732, 1697, 1367, 1240, 1157, 1063, 973, 756, 704 $cm^{-1}$±2 $cm^{-1}$.

15. A process for preparing the crystalline form of 13-[(N-tert-butoxycarbonyl)-2'-O-hexanoyl-3-phenylisoserinyl]-10-deacetylbaccatin III of claim 1, comprising the step of stirring 13-[(N-tert-butoxycarbonyl)-2'-O-hexanoyl-3-phenylisoserinyl]-10-deacetylbaccatin III in a mixture of an alcoholic solvent with water, and wherein the stirring time is at least 2 hours.

16. The process of claim 15, wherein 13-[(N-tert-butoxycarbonyl)-2'-O-hexanoyl-3-phenylisoserinyl]-10-deacetylbaccatin III, which is in the amorphous form, is at least partly dissolved in the alcoholic solvent, followed by mixing the alcoholic solution with water, and stirring the mixture of alcoholic solvent and water.

17. The process of claim 16, wherein the mixture is stirred at a temperature in the range of from 0 to 45° C. and wherein the alcoholic solvent comprises an alcoholic solvent chosen from the group consisting of methanol, ethanol, or a mixture thereof; and wherein the volumetric ratio alcoholic solvent and water is between 0.3 and 0.6.

* * * * *